United States Patent [19]

Morimoto et al.

[11] Patent Number: 5,723,660
[45] Date of Patent: Mar. 3, 1998

[54] PROCESS FOR PRODUCING ACETIC ACID

[75] Inventors: Yoshiaki Morimoto; Hiroyuki Nakayama, both of Niigata; Takashi Ueno, Hiroshima, all of Japan

[73] Assignee: Daicel Chemical Industries, Ltd., Osaka, Japan

[21] Appl. No.: 765,344

[22] PCT Filed: Apr. 22, 1996

[86] PCT No.: PCT/JP96/01087

§ 371 Date: Dec. 13, 1996

§ 102(e) Date: Dec. 13, 1996

[87] PCT Pub. No.: WO96/33965

PCT Pub. Date: Oct. 31, 1996

[30] Foreign Application Priority Data

Apr. 24, 1995 [JP] Japan ................... 7-104027

[51] Int. Cl.$^6$ ................ C07C 51/12; C07C 51/10
[52] U.S. Cl. ............................ 562/519; 562/517
[58] Field of Search ....................... 562/517, 519

[56] References Cited

U.S. PATENT DOCUMENTS 5,371,286 12/1994 Blay et al. ................... 562/519
5,599,976 2/1997 Scates et al. ................. 562/519
5,663,430 9/1997 Morris et al. ................. 562/608

FOREIGN PATENT DOCUMENTS

| 0 665 210 A1 | 8/1995 | European Pat. Off. . |
| 0 687 662 A2 | 12/1995 | European Pat. Off. . |
| 4-266843 | 9/1992 | Japan . |
| 4-295445 | 10/1992 | Japan . |
| 6-40999 | 2/1994 | Japan . |

*Primary Examiner*—Gary Geist
*Assistant Examiner*—Rosalynd Kap
*Attorney, Agent, or Firm*—Flynn, Thiel, Boutell & Tanis, P.C.

[57] ABSTRACT

The present invention provides a process for producing acetic acid by reacting continuously methanol, methyl acetate and the like with carbon monoxide in the presence of an eighth group metal-containing catalyst, methyl iodide and water, which is characterized in that wherein a liquid separation state in a decanter at the top of the first distillation column is maintained by adding water to the first distillation column. High quality acetic acid which has not so far been achieved can be obtained while controlling the purifying energy in a low level.

1 Claim, No Drawings

PROCESS FOR PRODUCING ACETIC ACID

This application is a 371 of PCT/JA96/01087, filed Apr. 22, 1996.

BACKGROUND OF THE INVENTION

1. Field of the Invention

The present invention relates to a novel process for producing acetic acid formed by carbonylating at least one selected from methanol, methyl acetate, and dimethyl ether in the presence of an eighth group metal-containing catalyst. More specifically, the present invention relates to a novel process for producing high purity acetic acid, wherein organic iodine compounds and carbonyl compounds which are impurities contained in the product are reduced in producing acetic acid formed by rhodium-catalyzed carbonylation while notably reducing energy necessary for purifying it.

2. Description of the Related Art

Acetic acid is used in large quantities as a raw material for acetic esters, acetic anhydride, vinyl acetate, and terephthalic acid and is an essential compound necessary for many industries including the polymer industry and the chemical industry.

Various processes are known as an industrial process for producing acetic acid. At present, a process in which methanol is continuously reacted with carbon monoxide in the presence of water using a rhodium catalyst and methyl iodide is widely employed as the industrial process for producing acetic acid (JP-B-47-3334).

According to a process for producing acetic acid by carbonylation of methanol, which is described in Applied Industrial Catalysis written by R. T. Eby and T. C. Singleton, vol. 1, pp. 275 to 296, 1983, crude acetic acid is purified by the continuous three distillation steps shown below. That is, (1) a low boiling components-separating column for separating low boiling components in the top part and high boiling components in the bottom part from side stream crude acetic acid in order to circulate them into a carbonylation reactor; (2) a dehydrating column for separating water from the side stream crude acetic acid withdrawn from the above column and circulating the separated water into the carbonylating reactor; and (3) a high boiling components-removing column for separating by-produced propionic acid from dried acetic acid. Since in this kind of process, a water content in a carbonylation reactor is as relatively high as 14 to 15 wt %, and a lot of propionic acid is by-produced, an enormous amount of purifying energy is necessary for obtaining product acetic acid.

In this process for producing acetic acid by carbonylation of methanol, the reaction conditions and a process for improving catalysts have recently been investigated, and for example, a process in which a catalyst stabilizer such as iodide salts is added is disclosed (JP-A-60-54334 and JP-A-60-239434). It is disclosed therein that the amounts of by-products such as carbon dioxide and propionic acid can be decreased by reducing a water content in a carbonylation reactor. Further, it is proposed that a purifying process for obtaining product acetic acid can be simplified by reducing a water content in a reactor (JP-A-6-040999). However, when the water content in the carbonylation reactor is decreased, the components which increase in amounts as the productivity of acetic acid grows and deteriorate the quality of product acetic acid are included in by-produced trace impurities. Components which particularly exert influences to some kind of applications are included as well in these trace impurities. For example, catalysts used for producing vinyl acetate from ethylene and acetic acid are very sensitive to these impurities (JP-A-4-282339). It is also known that impurities contained in acetic acid thus obtained are, to be concrete, carbonyl compounds such as acetaldehyde, crotonaldehyde and 2-ethylcrotonaldehyde, and organic iodine compounds such as hexyl iodide (JP-A-1-211548 and JP-B-5-21031). It is known as well that among the products shown above, the carbonyl compounds such as acetaldehyde, crotonaldehyde and 2-ethylcrotonaldehyde deteriorate assay values in a quality test by which the amounts of trace reductive impurities present in acetic acid are determined, which is called a permanganic acid reductive substance test (permanganic acid time) (JP-A-1-211548). A lot of investigations have been made for the purpose of removing these trace impurities formed in producing acetic acid by the carbonylation of methanol.

For example, it is known a process in which attentions are paid to the fact that a great part of these trace impurities originates in acetaldehyde produced during the reaction, and acetaldehyde is removed from a liquid in which acetaldehyde is concentrated in the process by distillation, extraction or reaction to thereby reduce the concentrations of trace impurities contained in product acetic acid (JP-A-4-266843). In these patents, however, nothing is referred to from the viewpoints of a simplification in a purifying process and a reduction in purifying energy. Further, according to the process described in JP-A-4-266843, caused is such a serious problem that nitriles by-produced in a conversion reaction of aldehydes to oximes accumulate in a carbonylation step.

SUMMARY OF THE INVENTION

Detailed Description of the Invention

The present invention provides a process for producing acetic acid by carbonylation of at least one selected from methanol, methyl acetate and dimethyl ether, wherein the concentrations of carbonyl compounds such as acetaldehyde, crotonaldehyde and 2-ethylcrotonaldehyde, and organic iodine compounds such as hexyl iodide which are contained in crude acetic acid as impurities are efficiently reduced while intending to simplify the purifying process thereof and reduce the purifying energy.

An object of the present invention is to overcome the defects and disadvantages of the prior arts brought about in producing acetic acid by a series of continuous production facilities.

The present inventors have paid attentions to the fact that carbonyl compounds such as acetaldehyde, crotonaldehyde and 2-ethylcrotonaldehyde, and organic iodine compounds such as hexyl iodide are by-produced in a step for producing acetic acid by carbonylation of methanol and the fact that among these by-products, carbonyl compounds such as crotonaldehyde and 2-ethylcrotonaldehyde, and organic iodine compounds such as hexyl iodide increase in by-production amounts by decreasing the amount of water contained in the carbonylation reaction liquid. Further, the present inventors have paid attentions to the facts that as the concentration of water contained in the carbonylation reaction liquid decreases or the concentration of methyl acetate contained in the reaction liquid increases, a liquid separability in the decanter at the top of the first distillation column is deteriorated and that all of a series of these impurities are components which are easy to form an azeotrope with water and the solubilities thereof in a methyl iodide phase are markedly high as compared with those in an aqueous phase.

That is, the present invention provides a process for producing acetic acid by reacting continuously at least one selected from methanol, methyl acetate and dimethyl ether with carbon monoxide in the presence of an eighth group metal-containing catalyst, methyl iodide and water, comprising:

(a) a step in which a crude reaction liquid is withdrawn from a carbonylation step and introduced into a flash zone, and a catalyst circulating liquid containing a catalyst component which is not evaporated in the flash zone is circulated into a carbonylation reactor, (b) a step in which a vapor fraction evaporated in the flash zone is fed into the first distillation column in the form of vapor and/or liquid, (c) a step in which a low boiling circulating stream comprising water, methyl acetate, methyl iodide, and acetic acid is withdrawn from the top of the first distillation column, and (d) a step in which crude acetic acid is withdrawn from the bottom or the side cut near the bottom of the first distillation column, characterized by that a liquid separation state in the decanter at the top of the first distillation column is maintained by adding water to the first distillation column, lowering a cooling temperature at the overhead part of the first distillation column, or reducing the concentration of methyl acetate contained in a liquid fed into the decanter at the top of the first distillation column to 40 wt % or less.

According to the present invention, while controlling the purifying energy in a lower level, the concentrations of impurities mixed in the product can be reduced particularly under the conditions that the concentration of water contained in the carbonylation reaction liquid.

First, the process for producing acetic acid by carbonylation of methanol according to the present invention will be explained.

The eighth group metal-containing catalyst used in the present invention includes the compounds of rhodium, iridium, ruthenium, osmium, cobalt, and nickel. The use form of the catalyst may be any one as long as it is soluble under the reaction conditions or can be converted to the soluble type. The form of the rhodium catalyst may be any one as long as it can form rhodium carbonyl complex species in the reaction system, and the non-limiting examples thereof include $RhX_3$ (wherein X represents Cl, Br or I), $RhX_3.3H_2O$ (wherein X represents Cl, Br or I), $Rh_2(CO)_{16}$, $Rh(CO)X[(C_6H_5)_3M]_2$ (wherein X represents Cl, Br or I, and M represents P, As or Sb ), $Rh(CO)_2X[(C_6H_5)_3M]$ (wherein X represents Cl, Br or I, and M represents P, As or Sb), $HRh(CO)[(C_6H_5)_3P]_3$, $[Rh(C_2H_4)_2Cl]_2$, $K_4Rh_2X_2(SnX_3)_4$ (wherein X represents Cl, Br or I) , and the rhodium components described in JP-B-47-3334. The concentration of rhodium contained in the reaction liquid is 200 to 1,000 ppm, preferably 300 to 600 ppm.

The non-limiting examples of the use form of the iridium catalyst include $IrX_3$ (wherein X represents Cl, Br or I), $[Ir(CO)_2X]_2$ (wherein X represents Cl, Br or I), $[Ir(CO)_2X_2]^-$ (wherein X represents Cl, Br or I), $[Ir(CH_3)X_3(CO)_2]^-$ (wherein X represents Cl, Br or I) , $Ir_4(CO)_{12}IrX_3.4H_2O$ (wherein X represents Cl, Br or I), $IrX_3.4H_2O$ (wherein X represents Cl, Br or I), $Ir_3(CO)_{12}$, iridium metal, $Ir_2O_3$, $IrO_2$, $Ir(acac)(CO)_2$, $Ir(acac) (CO)_3$, iridium acetate $[Ir_3O(OAc)_6(H_2O)_3][OAc]$, and $[H_2IrX_6]$ (wherein X represents Cl, Br or I) . Preferably included are, for example, halogen free complexes of iridium such as acetates, oxalates and acetoacetates. The concentration of iridium contained in the reaction liquid is 500 to 4,000 ppm, preferably 2,000 to 3,000 ppm.

The non-limiting examples of the use form of the ruthenium catalyst include $RuX_3$ (wherein X represents Cl, Br or I), $RuX_3.3H_2O$ (wherein X represents Cl, Br or I), ruthenium chloride (IV), ruthenium bromide (III), ruthenium metal, ruthenium oxide, ruthenium formate (III), $[Ru(CO)_3X_3]^-H^+$ (wherein X represents Cl, Br or I), tetra(aceto)chlororuthenium (II, III), ruthenium acetate (III), rutheniumpropionate (III), rutheniumbutyrate (III), ruthenium pentacarbonyl, triruthenium dodecacarbonyl and mixed rutheniumhalocarbonyl, for example, dichlorotricarbonyl ruthenium (II) dimer and dibromotricarbonyl ruthenium (II) dimer, and other organic ruthenium complexes, for example, tetrachlorobis(4-cymene)diruthenium (II), tetrachlorobis(benzene)diruthenium (II), dichloro-(cycloocta-1,5-diene) ruthenium (II) polymer, and tris-(acetylacetonate)ruthenium (III). The concentration of ruthenium contained in the reaction liquid is 500 to 4,000 ppm, preferably 2,000 to 3,000 ppm.

The non-limiting examples of the use form of the osmium catalyst include $OsX_3$ (wherein X represents Cl, Br or I), $OsX_3.3H_2O$ (wherein X represents Cl, Br or I), osmium metal, osmium tetraoxide, triosmium dodecacarbonyl, pentachloro-μ-nitrodiosmium, mixed osmium halocarbonyl, for example, tricarbonyl dichloroosmium (II) dimer, and other organic osmium Complexes. The concentration of osmium contained in the reaction liquid is 500 to 4,000 ppm, preferably 2,000 to 3,000 ppm.

These catalysts can be used singly or in combination of two or more kinds thereof. A case where the rhodium catalyst is used will be described below as one example.

In the present invention, iodide salts are added for stabilizing the rhodium catalyst particularly under low water and as a co-catalyst. This iodide salt may be any one as long as it generates iodine ions in a reaction liquid. The examples thereof include alkaline metal iodide salts such as LiI, NaI, KI, RbI and CsI, and alkaline earth metal iodide salts such as $BeI_2$, $MgI_2$ and $CaI_2$, and aluminum group metal iodide salts such as $BI_3$ and $AlI_3$. Organic iodide salts as well as the metal iodide salts can be used and include, for example, quaternary phosphonium iodides (methyl iodide abducts or hydrogen iodide adducts of tributyl phosphine and triphenyl phosphine), and quaternary ammonium iodides (methyl iodide adducts or hydrogen iodide adducts of tertiary amine, pyridines, imidazoles, and imides). In particular, the alkaline metal iodides such as LiI are preferred. The use amount of the iodide salts is 0.07 to 2.5 mole/liter, preferably 0.25 to 1.5 mole/liter in terms of an iodide ion in a reaction liquid. In the present invention, methyl iodide is used as a catalyst accelerator and allowed to be present in a reaction liquid in a proportion of 5 to 20 wt. %, preferably 12 to 16 wt. %. The concentration of water contained in the reaction liquid in the present process is 15 wt. % or less, preferably 8 wt. % or less, and more preferably 5 wt. % or less. Further, methyl acetate is present in a proportion of 0.1 to 30 wt. %, preferably 0.5 to 5. wt. %, and the balance of the principal components in the reaction liquid is acetic acid which is the product as well as the reaction solvent. When dimethyl ether and methyl acetate are used as raw materials, they react with carbon monoxide to form acetic anhydride and then promptly react with water to form acetic acid.

In the present invention, typical reaction temperatures in the carbonylation of methanol are from about 150° to 250° C. and fall preferably in a temperature range of from about 180° to 220° C. The overall reaction pressure is controlled within a range of from about 15 atm to 40 atm for the sake of the vapor pressures of the liquid components contained in the reactor, carbon monoxide partial pressure and hydrogen partial pressure.

The crude reaction liquid obtained by carrying out the carbonylation in the presence of the catalyst, the co-catalyst, the catalyst stabilizer and the reaction accelerator is withdrawn from the reactor and introduced into the flash zone. The flash zone is maintained preferably in a pressure of less than the carbonylation pressure, typically 1 to 6 atm. The flash zone is maintained at temperatures of 100° to 200° C. by heating or cooling or without heating or cooling.

A catalyst circulating liquid containing the catalyst components which are not evaporated in the flash zone is circulated into the carbonylation reactor as it is or, if necessary, after it is processed with hydrogen and carbon monoxide.

A vapor fraction evaporated in the flash zone is fed into the first distillation column in the form of vapor and/or liquid. The first distillation column can preferably be operated at almost the same pressure as that of the flash zone and can be operated as well at a higher or lower pressure. Operating temperatures of the first distillation column are influenced by the composition of components fed, the operating pressure, the number of stages, and the reflux amount.

The concentration of water contained in the carbonylation reaction liquid is preferably lower from the viewpoint of controlling the by-production amount of propionic acid and the by-production amount of carbon dioxide formed by a shift reaction. However, as the concentration of water contained in the carbonylation reaction liquid is lowered, the liquid separability in the decanter at the top of the first distillation column is deteriorated, and the separation stops in a short time. As a result thereof, impurities which are driven up to the top of the first distillation column by water refluxed into the top of the distillation column when the concentration of water contained in the carbonylation reaction liquid is high are liable to mix into crude acetic acid withdrawn from the bottom or the side cut near the bottom of the first distillation column due to a reduction in the concentration of water.

In separating the liquid in the decanter at the top of the first distillation column, the liquid is separated into two phases of a phase comprising mainly methyl iodide (hereinafter referred to as a methyl iodide phase) and a phase comprising mainly water (hereinafter referred to as an aqueous phase). The methyl iodide phase in which a lot of impurities are dissolved is withdrawn as a low boiling circulating stream, but after the separation stops, a part of the liquid containing the impurities is fed to the first distillation column as a refluxing liquid, and therefore the impurities are liable to mix into crude acetic acid.

The present invention provides a process in which the concentrations of the impurities contained in crude acetic acid withdrawn from the bottom or the side cut near the bottom of the first distillation column are suppressed to a lower level when the concentration of water contained in the carbonylation reaction liquid is reduced to such an extent that the separability at the top of the first distillation column is deteriorated in conventional processes. In particular, it is applied when the concentration of water contained in the carbonylation reaction liquid is reduced to 8 wt. % or less. In such case, the following methods are given as a measure for maintaining the separability.

These methods are particularly effective for maintaining the separability when the concentration of methyl acetate contained in the reaction liquid is maintained in such a high level as about 2 wt. % or more in order to obtain the high activity, that is, when the concentration of methyl acetate in the overhead part of the first distillation column is raised to such a high level as about 6 wt. % or more.

(1) Water is fed batchwise into the first distillation column.
(2) Crude acetic acid withdrawn from the side stream at the bottom of the first distillation column or in the vicinity of the bottom thereof is fed into the second distillation column, or water is batchwise added, if necessary, to the crude acetic acid described above to feed it into the second distillation column; water is separated by fractional distillation in the second distillation column, and a liquid which is fractionated at the top of the second distillation column is steadily circulated into the first distillation column; water may be added to the liquid fractionated at the top of the second distillation column to steadily circulate it into the first distillation column; the liquid fractionated at the top of the second distillation column is allowed to contain acetic acid; when the operation is carried out according to these methods, the amount of an upper phase (aqueous phase) refluxed from the decanter at the top of the first distillation column and the flow amount of the bottom or the side cut near the bottom of the first distillation column are preferably increased so that water added is circulated between the first distillation column and the second distillation column.
(3) Cooling temperatures at the top of the first distillation column are lowered; the optimum cooling temperature can be selected in a range of −40° to 60° C., preferably −20° to 40° C.

As a matter of course, the methods described above may be used singly or in combination of a plurality thereof as means for maintaining the separability in the decanter at the top of the first distillation column. Further, the separability may be maintained by increasing the number of the stages in the distillation column or enhancing the refluxing amount in the decanter at the top of the first distillation column.

Further, the means for maintaining the separability includes a method in which the concentration of methyl acetate contained in the liquid fed to the decanter at the top of the first distillation column is lowered down to 40 wt. % or less. To be concrete, for example, a methyl acetate mixture is separated from a low boiling circulating liquid or overhead vapor withdrawn from the top of the first distillation column in the third distillation column, and further in the fourth and fifth distillation columns, if necessary. The methyl acetate mixture is returned to the reaction process, and the liquid which has decreased in the concentration of methyl acetate is fed to the decanter at the top, whereby the separability can be maintained.

Only the upper phase (aqueous phase) obtained by fractionating these two phases is preferably used for the reflux to the first distillation column. The lower the cooling temperatures at the top of the first distillation column are, and/or the more the refluxing amount to the first distillation column increases, or the more the number of stages in the distillation column increases, the better the separability can be maintained even if the amount of water to be further fed is decreased.

A low boiling circulating liquid comprising the upper phase (aqueous phase) and the lower phase (methyl iodide phase) is withdrawn from the top of the first distillation column and circulated into the carbonylation reactor as it is or after removing acetaldehyde out of the system by a known method, that is, distillation, extraction or reaction.

Crude acetic acid withdrawn from the bottom or the side cut near the bottom of the second distillation column may be product acetic acid as it is, or may be subjected to known distillation operation, treatment by contact with strong acid cation exchange resins exchanged with silver, oxidation treatment, treatment with alkaline metal salts, treatment with silver compounds, or treatment with methyl acetate and methanol.

The present invention can be applied to various processes such as a process in which a crude acetic acid product obtained in producing acetic acid by carbonylation is purified in continuous three distillation steps, that is, (1) a low boiling component-separating column in which a low boiling component at the top part of the column is separated from crude acetic acid, (2) a dehydrating column in which water is separated from the crude acetic acid withdrawn from the above column, and (3) a high boiling component-removing column in which by-produced propionic acid is separated from dried acetic acid, and a process in which the process described above is simplified and the purification is carried out in one or two distillation columns.

Effect of the Invention

According to the present invention, acetic acid of a high quality which has not so far been able to achieve can be obtained by maintaining the separability at the top of the first distillation column under the conditions that the concentration of water contained in the carbonylation reactor is lowered while controlling purifying energy to a lower level.

Examples

The present invention will be explained below with reference to examples, but the present invention shall not be limited by these examples.

Comparative Example 1

A crude reaction liquid comprising acetaldehyde of 1200 ppm, methyl iodide of 14 wt. %, water of 2.5 wt. %, methyl acetate of 2.0 wt. %, acetic acid of 60.5 wt. %, lithium iodide of 20 wt. %, and rhodium (prepared from $RhI_3$) of 400 ppm was introduced from a continuous withdrawal type autoclave (carbonylation reactor) of 1000 ml maintained at 187° C. and 28 atm into a flash zone maintained at 2.3 atm and 153° C. A catalyst circulating liquid containing a catalyst component which was not evaporated in the flash zone was withdrawn from thbottom of the flash zone and circulated into a carbonylation reactor with a high pressure pump. A component comprising primarily resulting acetic acid, methyl iodide which was a co-catalyst, methyl acetate, and water was withdrawn from the top of the flash zone and introduced into the first distillation column, and methyl iodide, methyl acetate, and water which were low boiling components were separated from acetic acid which was a high boiling component. An Auldershow distillation column consisting of 20 stages was used for the first distillation column. A liquid withdrawn from the top of the first distillation column did not separate. The distillate withdrawn from the first distillation column was circulated into the carbonylation reactor, and crude acetic acid was obtained from a side stream withdrawn from the first distillation column. Carbonyl impurities contained in the above crude acetic acid were converted into the derivatives with dinitrophenyl hydrazine and then analyzed with liquid chromatography to find that the carbonyl impurities were contained in the crude acetic acid in large quantities. Since the impurities were contained in too large quantities, they were not determined.

Example 1

Water was batchwise added (the amount of water added batchwise corresponded to 0.8 wt. part per 100 wt. parts of the mixture fed from the top in the flash zone to the first distillation column) to crude acetic acid obtained from the side stream withdrawn from the first distillation column shown in Comparative Example 1, and the crude acetic acid was fed to the second distillation column. In the second distillation column, water was separated from the top part and circulated into the first distillation column. In the first distillation column, the refluxing amount of the upper phase (aqueous phase) withdrawn from the decanter at the top of the first distillation column was increased so that water corresponding to a combined amount of water mixed in the side stream crude acetic acid obtained in Comparative Example 1 and water added in the present example was mixed into side stream acetic acid. The refluxing amount (continuous) was 65 to 63 wt. parts per 100 wt. parts of the mixture fed into the first distillation column. That is, the refluxing amount of the upper phase (aqueous phase) withdrawn from the decanter at the top of the first distillation column was adjusted so that water added was circulated from the first distillation column to the second distillation column without circulating into the carbonylation reactor. Carbonyl impurities contained in crude acetic acid thus obtained from the side cut withdrawn from the first distillation column were converted into the derivatives by dinitrophenyl hydrazine and then determined with liquid chromatography. Hexyl iodide was analyzed with SIM-GC. As a result thereof, it was found that crotonaldehyde of 110 ppm, 2-ethylcrotonaldehyde of 200 ppm, and hexyl chloride of 4 ppm in addition to water of 2.2 wt. % were contained.

Comparative Example 2

The same procedure as that in Comparative Example 1 was repeated, except that the composition of the crude reaction liquid was changed to water of 2.0 wt. %, methyl acetate of 5.0 wt. %, and acetic acid of 58.0 wt. %, but the liquid withdrawn from the top (decanter temperature was 40° C.) of the first distillation column did not separate. The content of crotonaldehyde contained in crude acetic acid obtained from the side stream withdrawn from the first distillation column was 400 ppm or more.

Example 2

The same procedure as that in Comparative Example 2 was repeated, except that the temperature of the decanter at the top of the first distillation column was changed to 20° C., and the liquid withdrawn from the top of the first distillation column separated. The contents of crotonaldehyde and hexyl iodide contained in crude acetic acid obtained from the side stream withdrawn from the first distillation column were 250 ppm and 12 ppm, respectively.

Comparative Example 3

The same procedure as that in Comparative Example 1 was repeated, except that the crude reaction liquid comprising acetaldehyde of 175 ppm, methyl iodide of 5 wt. %, water of 7.0 wt. %, methyl acetate of 15 wt. %, acetic acid of 72 wt. %, iridium and ruthenium (prepared from $IrI_3$ and $RuI_3$) of 4,000 ppm was used, but the liquid withdrawn from the top (decanter temperature was 40° C.) of the first distillation column did not separate. The content of crotonaldehyde contained in crude acetic acid obtained from the side stream withdrawn from the first distillation column was 10 ppm or more.

The temperature of the decanter was lowered down to −5° C. but the liquid did not separate. The temperature was further lowered, and the liquid started freezing at −10° C., which made the operation impossible.

Example 3

Crude acetic acid obtained from the side stream withdrawn from the first distillation column shown in Comparative Example 3 (decanter temperature: 40° C.) was fed to the second distillation column. Water was batchwise added (the amount of water added batchwise corresponded to 2 wt. parts per 100 wt. parts of the mixture fed from the top in the flash zone to the first distillation column) to a fractional liquid withdrawn from the top of the second distillation column, and the liquid was circulated to the first distillation column. The refluxing amount of the upper phase (aqueous phase) withdrawn from the decanter at the top of the first distillation column was controlled so that water added was circulated from the first distillation column to the second distillation column without circulating into the carbonylation reactor. The content of crotonaldehyde contained in crude acetic acid thus obtained from the side stream withdrawn from the first distillation column was 3 ppm.

Example 4

Example 4 is to show that the liquid separates in the decanter by reducing the concentration of methyl acetate contained in the liquid fed to the decanter at the top of the first distillation column.

In Comparative Example 3, the distillate (low boiling circulating liquid) withdrawn from the top of the first distillation column was analyzed to find that the concentration of methyl acetate was 55 wt. %.

This distillate (low boiling circulating liquid) was fed to the third distillation column and processed. The Auldershow distillation column consisting of 20 stages was used for the third distillation column. A liquid containing methyl iodide as a main component was withdrawn from the top in an amount of 35 wt. parts per 100 wt. parts of the charged amount and introduced into the decanter. A charging stage in the third distillation column resided in the central part, and the operation was carried out at a reflux ratio of 1. The liquid of remaining 65 wt. parts was withdrawn from the bottom of the column and fed into the fourth distillation column. The Auldershow distillation column consisting of 20 stages was used for the fourth distillation column. A liquid containing methyl acetate as a main component was withdrawn from the top in an amount of 31 wt. parts per 100 wt. parts of the charged amount and introduced into the carbonylation reactor. A charging stage in the forth distillation column resided in a position which was ¼ over the bottom of the column, and the operation was carried out at a reflux ratio of 1. The liquid of remaining 69 wt. parts was withdrawn from the bottom of the column and fed into the decanter. Two kinds of the liquids fed to the decanter were analyzed to determine the mixed composition of these liquids. The composition thereof comprised methyl acetate of 17 wt. %, methyl iodide of 30 wt. %, and water of 25 wt. %, and it could be confirmed that the liquid separated in the decanter. The temperature of the decanter was 40° C. The content of crotonaldehyde contained in crude acetic acid obtained from the side stream withdrawn from the first distillation column was 2 ppm.

Further, in the fourth distillation column, the methyl acetate mixed liquid withdrawn from the top was reduced down to 26 wt. parts while maintaining the reflux ratio of 1. The mixed composition of two kinds of the liquids comprised methyl acetate 30 wt. %, methyl iodide of 35 wt. %, and water of 17 wt. %, and it could be confirmed that the liquid separated in the decanter at an operating temperature of 40° C.

We claim:

1. A process for producing acetic acid by reacting continuously at least one selected from methanol, methyl acetate and dimethyl ether with carbon monoxide in the presence of an eighth group metal-containing catalyst, methyl iodide and water, comprising:
   (a) a step in which a crude reaction liquid is withdrawn from a carbonylation step and introduced into a flash zone, and a catalyst circulating liquid containing a catalyst component which is not evaporated in the flash zone is circulated into a carbonylation reactor,
   (b) a step in which a vapor fraction evaporated in the flash zone is fed into a first distillation column in the form of vapor and/or liquid,
   (c) a step in which a low boiling circulating stream comprising water, methyl acetate, methyl iodide, and acetic acid is withdrawn from the top of the first distillation column, and
   (d) a step in which crude acetic acid is withdrawn from the bottom or the side cut near the bottom of the first distillation column, wherein a liquid separation state in a decanter at the top of the first distillation column is maintained by reducing the concentration of methyl acetate contained in a liquid fed into the decanter at the top of the first distillation column to 40 wt % or less.

\* \* \* \* \*

UNITED STATES PATENT AND TRADEMARK OFFICE
CERTIFICATE OF CORRECTION

PATENT NO. : 5 723 660
DATED : March 3, 1998
INVENTOR(S) : Yoshiaki MORIMOTO et al It is certified that error appears in the above-indentified patent and that said Letters Patent is hereby corrected as shown below:

On title page, item [56], under Foreign Application Priority Data, change "April 24, 1995" to ---April 27, 1995---.

Signed and Sealed this

Twenty-first Day of July, 1998

Attest:

BRUCE LEHMAN

*Attesting Officer*     *Commissioner of Patents and Trademarks*